US005849999A

United States Patent [19]
Neve et al.

[11] Patent Number: 5,849,999
[45] Date of Patent: Dec. 15, 1998

[54] TRANSGENIC NON-HUMAN MICE EXPRESSING FLAG-APP-C100 PROTEIN DEVELOP ALZHEIMER'S DISEASE BRAIN MORPHOLOGY AND BEHAVIOR

[75] Inventors: Rachael L. Neve, Belmont; Joanne Berger-Sweeney, Natick, both of Mass.

[73] Assignees: The McLean Hospital Corporation, Belmont; Wellesley College, Wellesley, both of Mass.

[21] Appl. No.: 729,345

[22] Filed: Oct. 16, 1996

[51] Int. Cl.$^6$ .............................. C12N 5/00; C12N 15/00; A61K 49/00

[52] U.S. Cl. ......................... 800/2; 800/DIG. 1; 424/9.1; 435/172.3; 935/60

[58] Field of Search .................................. 800/2, DIG. 1; 935/60; 435/172.3, 320.1; 536/23.1; 424/9.1

[56] References Cited

U.S. PATENT DOCUMENTS

| | | | |
|---|---|---|---|
| 5,011,912 | 4/1991 | Hopp et al. | 530/387 |
| 5,387,742 | 2/1995 | Cordell | 800/2 |
| 5,554,512 | 9/1996 | Lyman et al. | 435/69.5 |

FOREIGN PATENT DOCUMENTS

| | | |
|---|---|---|
| 0451 700 A1 | 10/1991 | European Pat. Off. . |
| WO 89/06689 | 7/1989 | WIPO . |
| WO 90/05138 | 5/1990 | WIPO . |
| WO 91/19810 | 12/1991 | WIPO . |
| WO 92/06187 | 4/1992 | WIPO . |
| WO 93/02189 | 2/1993 | WIPO . |

OTHER PUBLICATIONS

Arters et al., Abstract. DD–41 1:00 579.9 "Sex Dependent Cognitive Impairments in Transgenic Mice that Overexpress the Carboxy–Terminal Fragment . . . Precursor Peptide", (APP–C100) Soc. Neurosci. Abs. 25: 1995.

Benowitz et al., "The Amyloid Precursor Protein Is Concentrated in Neuronal Lysosomes in Normal and Alzheimer Disease Subjects", Experimental Neurology 106:237–250, 1989.

Boyce et al., "Dystrophin is Transcribed in Brain From A Distant Upstream Promoter", Proc. Natl. Acad. Sci. USA 88:1276–1280, 1991.

Carpenter et al., "Morphometric Analysis of Microglia Alzheimer's Disease", J. Neuropathol. Exp. Neurol. 52:601–608, 1993.

Cataldo et al., "Lysomal Abnormalities in Degenerating Neruons Link Neuronal Compromise to Senile Plaque Development in Alzheimer Disease", Brain Research 640:68–80, 1994.

DeKosky et al., "Synapse Loss in Frontal Cortex Biopsies in Alzheimer's Disease: Correlation with Cognitive Severity", Annals of Neurology 27:457–464, 1990.

Estus et al., "Potentially Amyloidogenic Carboxyl–Terminal Derivatives of the Amyloid Protein Precursor" Science 255:726–728, 1992.

Fukuchi et al., "Overexpression of a C–Terminal Portion of the β–Amyloid Precursor Protein in Mouse Brains by Transplantation of Tramsformed Neuronal Cells", Experimental Neurology 127:253–264, 1994.

Fukuchi et al., "Overexpress of Amyloid Precursor Protein Alters Its Normal Processing And Is Associated With Neurotoxicity", Biochem. and Biophys. Res. Communications 182:165–173.

Fukuchi et al., "Selective Neurotoxicity of COOH–Terminal Fragments of the β–Amyloid Precursor Protein", Neuroscience Letters 154:145–148, 1993.

Hamos et al., "Synaptic Loss In Alzheimer's Disease And Other Dementias", Neurology 39:355–361, 1989.

Kalaria, "The Blood–Brain Barrier and Cerebral Microcirculation in Alzheimer Disease", Cerebrovascular and Brain Metabolism Reviews 4:226–260, 1992.

Kammesheidt et al., "Deposition of β/A4 Immunoreactivity and Neuronal Pathology in Transgenic Mice Expressing the Carboxyl–Terminal Fragment . . . Brain" Proc. Natl. Acad. Sci. USA 89:10857–10861, 1992.

Kang et al., "The Precursor of Alzheimer's Disease Amyloid A4 Protein Resembles A Cell–Surface Receptor" Nature 325:733–736, 1987.

Kozlowski et al., "The Neurotoxic Carboxy–Terminal Fragment of the Alzheimer Amyloid Precursor Binds Specifically to a Neuronal Cell Surface Molecule: . . . and the Binding" J. Neurosci. 12:1679–1687, 1992.

Lynn et al., "Propagation of Intercellular Calcium Waves in PC12 Cells Overexpressing a Carboxy–Terminal Fragment of Amyloid Precursor Protein" Neurosci. Letters 199:21–24, 1995.

Marotta et al., "Overexpression of Amyloid Precursor Protein A4 (β–Amyloid) Immunoreactivity in Genetically Transformed Cells" Proc. Natl. Acad. Sci. USA 86:337–341, 1989.

Neve et al., "Brain Transplants of Cells Expressing The Carboxyl–Terminal Fragment of the Alzheimer Amyloid Protein Precursor Cause Specific Neuropathology in vivo", Proc. Natl. Acad. Sci. USA 89:3448–3452, 1992.

Neve et al., "Construction and Analysis of Transgenic Mice Expressing Amyloidogenic Fragments of Alzheimer Amyloid Protein Precursor" Meth. in Neurosci. 30:298–314, 1996.

(List continued on next page.)

*Primary Examiner*—Deborah Crouch
*Attorney, Agent, or Firm*—Fish & Richardson P.C.

[57] ABSTRACT

Disclosed is a transgenic non-human mammal that expresses in its brain a transgene encoding an APP-C100 polypeptide with the flag amino acid sequence fused to the amino terminus of the APP-C100. This transgenic non-human mammal is an improved in vivo model for Alzheimer's disease-like neuropathology and associated cognitive impairment. The improvement includes accelerated development of AD-like neuropathology and cognitive impairment. The AD-like neurodegeneration and associated cognitive impairment in mice produced according to this invention appear at least six months sooner than they appear in APP-C100-expressing transgenic mice.

11 Claims, 4 Drawing Sheets

OTHER PUBLICATIONS

Perlmutter et al., "Vascular Basement Membrane Components and the Lesions of Alzheimer's Disease: Light and Electron Microscopic Analyses", Microscopy Research and Technique 28:204–215, 1994.

Prickett et al., "A Calcium–Dependent Antibody for Identification and Purification of Recombinant Proteins" BioTechniques 7:580–589, 1989.

Quon et al., "Formation of β–Amyloid Protein Deposits in Brains of Transgenic Mice", Letters to Nature 352:239–241, 1991.

Sopher et al., "Cytotoxicity Mediated By Conditional Expression of a Carboxyl–Terminal Derivative of the β–Amyloid Precursor Protein", Molecular Brain Research 26:207–217, 1994.

Tate et al., "Disruption of Circadian Regulation by Brain Grafts that Overexpress Alzheimer β/A4 Amyloid" Proc. Natl. Acad. Sci. USA 89:7090–7094, 1992.

Terry et al., "Some Morphometric Aspects of the Brain in Senile Dementia of the Alzheimer Type", Annals of Neurology 10:184–192, 1981.

Terry et al., "Physical Basis of Cognitive Alterations in Alzheimer's Disease: Synapse Loss Is the Major Correlate of Cognitive Impairment", Annals of Neurology 30:572–580, 1991.

Vickers et al., "Alterations in Neurofilament Protein Immunoreactivity in Human Hippocampal Neurons Related To Normal Aging and Alzheimer's Disease", Neuroscience 62:1–13, 1994.

Wolozin et al., "A Neuronal Antigen in the Brains of Alzheimer Patients", Science 232:648–650, 1986.

Yankner et al., "Neurotoxicity of a Fragment of the Amyloid Precursor Associated With Alzheimer's Disease", Science 245:417–420, 1989.

Yoshikawa et al., "Degeneration In Vitro of Post–Mitotic Neurons Overexpressing the Alzheimer Amyloid Protein Precursor", Nature 359:64–67, 1992.

Lannfelt et al (1993) Behav. Brain Res. 57, 207–213.

Felsenstein (1995) Alzheimers Parkinson's Disease, ed. by P. Hanen et al, Plenum Press NY, 401–409.

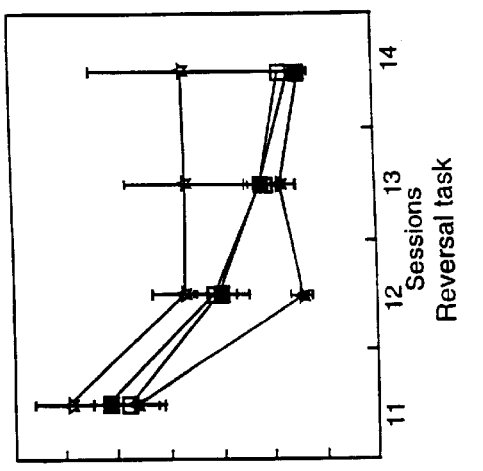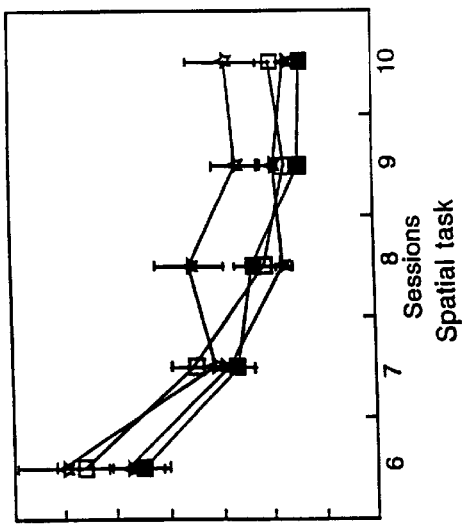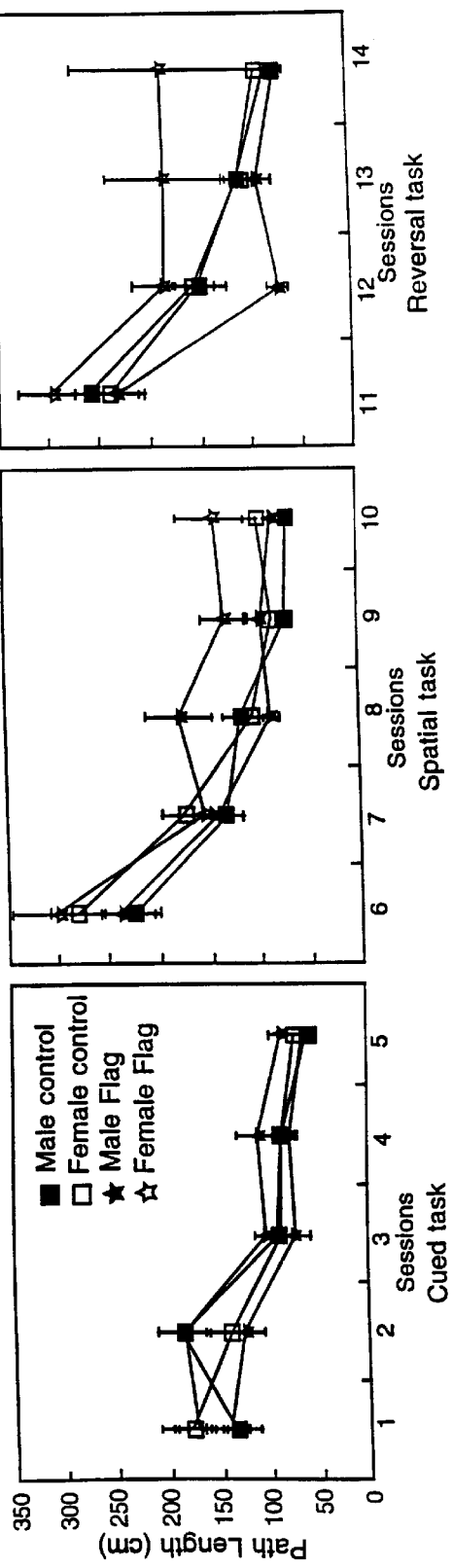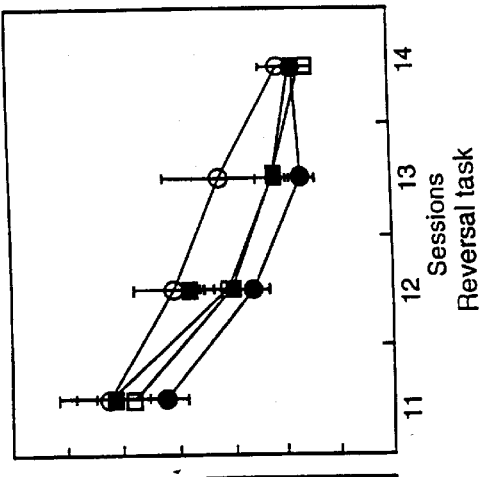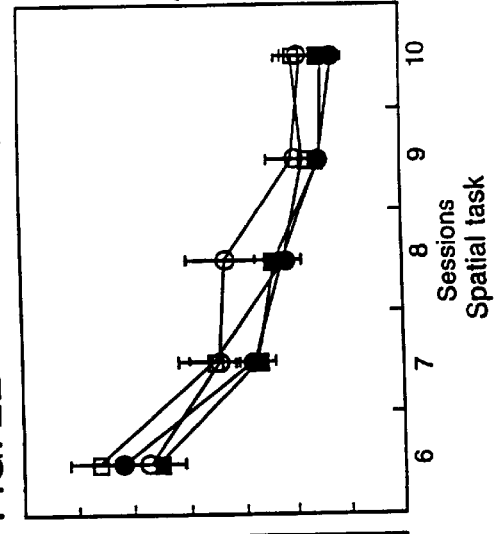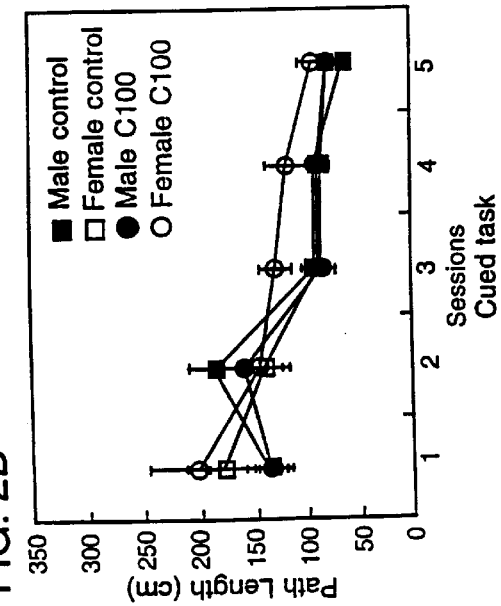

TRANSGENIC NON-HUMAN MICE EXPRESSING FLAG-APP-C100 PROTEIN DEVELOP ALZHEIMER'S DISEASE BRAIN MORPHOLOGY AND BEHAVIOR

STATEMENT AS TO FEDERALLY SPONSORED RESEARCH

Work on this invention was supported, in part, with funds from the United States government (NIH grants HD 19932 and AG 12954, and NSF grant IBN 9458101). The government therefore has certain rights in the invention.

BACKGROUND OF THE INVENTION

All individuals with Alzheimer's disease (AD) experience a progressive and specific loss of cognitive function, resulting from a neurodegenerative process. Typically, the neurodegenerative process is characterized by granulovacuolar degeneration, the deposition of amyloid in plaques and in the cerebrovasculature, and formation of neurofibrillary tangles in neurons. Additional pathological hallmarks of AD include degeneration of synapses (Terry et al., Ann. Neurol. 30:572–580 (1990); DeKosky et al., Ann. Neurol. 27:457–464 (1990); Hamos et al., Neurology 39:355–361 (1989) and decreases in cell density (Terry et al., Ann. Neurol. 10:184–192) (1981) in distinct regions of the brain, lysosomal abnormalities (Benowitz et al., Exptl. Neurol. 106:237–250 (1989); Cataldo et al., Brain Res. 640:68–80 (1994), proliferation of activated microglia (Carpenter et al., J. Neuropathol. Exp. Neurol. 52:601–608 (1993)), alterations of vascular basement membrane (Kalaria, Cerebrovasc Brain Metab. Rev. 4:226–260 (1992); Perlmutter et al., Microsc. Res. Tech. 28:204–215 (1994)), increases in the levels of neurofilament proteins (Vickers et al., Neuroscience 62:1–13 (1994)), and appearance of the Alz-50 antigen (Wolozin et al., Science 232:648–650 (1986)).

The carboxyl-terminal 100-amino acid fragment of the amyloid protein precursor (APP-C100), which includes the 42-amino acid Aβ peptide and 58 adjacent amino acids, is instrumental in causing AD neuropathology. This fragment is toxic to neuronal cells (Yankner et al., Science 245:417–420 (1989); Fukuchi et al., Neurosci. Let. 154:145–148 (1993); Sopher et al., Mol. Brain Res. 26:207–217 (1994)). Overexpression of normal APP (as occurs in Down syndrome, which is a predictor of AD neuropathology) can lead to the generation of APP-C100-like C-terminal fragments of APP and the death of the neuronal cells synthesizing these fragments in vitro (Fukuchi et al., Biochem. Biophys. Res. Commun. 182:165–173 (1992); Yoshikawa et al., Nature 359:64–67 (1992)), and to the deposition of extracellular Aβ in vivo (Quon et al., Nature 352:239–241 (1991)).

Transplantation of APP-C100-expressing PC12 cells into mouse brain causes severe cortical atrophy and abnormal Alz-50 immunostaining (Neve et al., Proc. Natl. Acad. Sci USA 89:3448–3452 (1992)). Similarly, transplantation of differentiated P19 cells stably transfected with C100 into mouse brains causes distortion and shrinkage in the hippocampus around the site of the transplant, and β-amyloid immunoreactivity in blood vessel walls and in the neuropil surrounding the site of the transplant (Fukuchi et al., Exptl. Neurol. 127:253–264 (1994)).

A murine model for Alzheimer's disease has been engineered for brain-specific expression of a transgene encoding APP-C100(WO 93/02189; Neve et al., Meth. Neurosci. 30:298–314 (1996); Kammesheidt et al., Proc. Natl. Acad. Sci. USA 89:10857–10861 (1992)). This APP-C100-based murine model exhibits degeneration of neurons and synapses in Ammon's horn and the dentate gyrus of the hippocampal formation.

SUMMARY OF THE INVENTION

It has been discovered that when the Flag sequence, i.e., Asp-Tyr-Lys-Asp-Asp-Asp-Asp-Lys (SEQ ID NO:4), is fused to the amino terminus of an APP-C100 polypeptide, and the fusion polypeptide is expressed in transgenic mice, the mice exhibit severe neurodegeneration of neurons and synapses in the hippocampal formation, and they also exhibit cognitive impairment, by twelve months of age. These AD-like features appear in the Flag-APP-C100 mice at least six months earlier than they appear in transgenic mice expressing the APP-C100polypeptide without the Flag sequence. Based on this discovery, the invention provides a transgenic nonhuman mammalian AD model that shortens the time required for drug screening, drug testing, or other research involving an in vivo AD model.

The transgenic nonhuman mammal contains a transgene encoding a Flag-APP-C100 polypeptide. The Flag-APP-C100 polypeptide includes a Flag peptide (SEQ ID NO:4) fused to the amino terminus of an APP-C100 polypeptide, with 0 to 5 intervening amino acid residues. The APP-C100 polypeptide can consist of the carboxy-terminal 100 to 105 amino acids of APP695 (SEQ ID NO:1). Preferably, Flag-APP-C100 polypeptide consists of (SEQ ID NO:3). The recombinant DNA sequence encoding the Flag-APP-C100 polypeptide can be, for example (SEQ ID NO:2). Preferably, the recombinant DNA sequence is operatively linked to expression control sequences. The expression control sequences preferably include a brain-specific promoter. The brain specific promoter can be, for example, a dystrophin promoter. Typically, the transgenic nonhuman mammal is a mouse.

The invention also features a method of enhancing neurodegeneration in the brain of a transgenic non-human mammalian AD model. The method includes the steps of: (a) obtaining an isolated DNA molecule encoding a polypeptide comprising a Flag peptide fused to the amino terminus of an APP-C100polypeptide, with 0 to 5 intervening amino acid residues; (b) introducing the DNA molecule into the mammal, or an ancestor of said mammal, at an embryonic stage, thereby producing a transgenic embryo; (c) providing for the embryo to develop into the mammal, which has a brain with enhanced neurodegeneration.

The invention also features an in vivo screening method for identifying a compound that inhibits neurodegeneration or cognitive impairment in AD. The method includes the steps of: (a) providing a transgenic nonhuman mammal containing a recombinant DNA sequence encoding a polypeptide comprising a Flag peptide fused to the amino terminus of an APP-C100polypeptide, with 0 to 5 intervening amino acid residues, (b) administering to the mammal a candidate compound; (c) detecting a decrease in neurodegeneration or cognitive impairment in the brain of the mammal compared to neurodegeneration in the brain of a control.

After a compound has been identified as having a desired in vivo activity, the non-human mammal of this invention can be used for pre-clinical drug testing. The transgenic non-human animal of this invention can also be used as an experimentally manipulable tool for elucidation of AD and AD-like disease mechanisms.

As used herein, "APP" means amyloid precursor protein (APP695).

As used herein, "APP-C100 polypeptide" means the carboxy-terminal 100 to 105 amino acids of APP695. An APP-C100 polypeptide optionally includes a methionine residue at its amino terminus.

As used herein, "APP-C100 mouse" means a transgenic mouse expressing a recombinant APP-C100 polypeptide in its brain.

As used herein, "control" mammal means a non-transgenic mammal of the same species as, and otherwise comparable to (e.g., similar age), a transgenic non-human mammal. A control mammal is the basis for comparison, in assessing results associated with a particular genotype.

As used herein, "Flag peptide" means Asp-Tyr-Lys-Asp-Asp-Asp-Asp-Lys (SEQ ID NO:4).

As used herein, "Flag-APP-C100 polypeptide" means a Flag peptide fused to the amino terminus of an APP-C100 polypeptide, with 0 to 5 intervening amino acid residues. A Flag-APP-C100 polypeptide optionally includes a methionine residue at its amino terminus.

As used herein, "Flag-APP-C100 mouse" means a transgenic mouse expressing a recombinant Flag-APP-C100 polypeptide in its brain.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present document, including definitions, will control. Unless otherwise indicated, materials, methods, and examples described herein are illustrative only and not intended to be limiting.

Various features and advantages of the invention will be apparent from the following detailed description and from the claims.

BRIEF DESCRIPTION OF THE DRAWINGS

FIGS. 2A–2C are graphs showing mean path lengths of non-transgenic control mice and Flag-APP-C100 mice on different sessions of a cued task, spatial task, and reversal task, respectively. Closed squares, male control; open squares, female control; closed stars male Flag-APP-C100; open stars female Flag-APP-C100. The * indicates statistical significance at $p<0.05$ (ANOVA).

FIGS. 2D–2F are graphs showing mean path lengths of non-transgenic control mice and APP-C100 mice on different sessions of a cued task, spatial task, and reversal task, respectively. Closed squares, male control; open squares, female control; closed circles male APP-C100; open circles, female APP-C100.

DETAILED DESCRIPTION

Figure 1A:
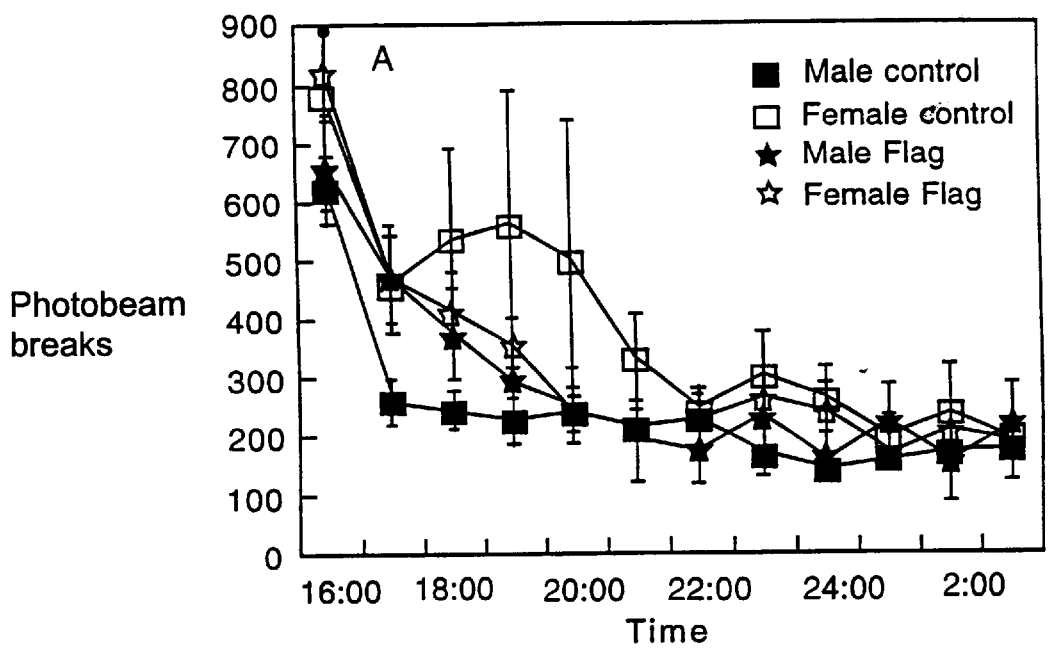
FIG. 1A is a graph showing data on spontaneous locomotor activity of control and Flag-APP-C100 mice. The number of photobeam breaks made over a 12-hour period is shown. Closed squares, male control; open squares, female control; closed stars male Flag-APP-C100; open stars female Flag-APP-C100.

Production of APP-C100 Mice APP-C100 mice were produced as described in Kammesheidt et al. (supra). The BglII-SmaI fragment of the βAPP-695 cDNA (basepairs 1769 to 2959 according to the sequence of Kang et al. (*Nature* 325:733 (1987)) was cloned into a modified form of pRSV β-globin (Gorman et al., *Science* 221:877 (1987)) in which the β-globin coding sequence had been replaced with a polylinker. The RSV promoter was replaced with the dystrophin neural promoter (Boyce et al., *Proc. Natl. Acad. Sci. USA* 88:1276 (1991)) by subcloning the latter (a 3-kb HindIII fragment) into MluI-HindIII-digested PRSVβAPP-C105 in which the MluI cohesive end had been filled in and ligated with HindIII linkers designed to retain the MluI site. The APP-C104 transgene, together with the upstream dystrophin promoter and the downstream SV40 splice and polyadenylation sequences, was excised from the plasmid sequences by digestion with MluI and BamHI. The DNA fragments were separated by agarose gel electrophoresis, and the transgene DNA fragment was electroeluted and ethanol precipitated. DNA concentration was determined by $OD_{260}$. DNA was microinjected into the pronuclei of fertilized eggs from F2 hybrid mice (C57BL/6J×SJL/J) at DNX (Princeton, N.J.) using conventional techniques. The injected mouse eggs were reimplanted into pseudopregnant recipient females.

Production of Flag-APP-C100 Mice

The Flag-APP-C100 transgenic mice were identical to the APP-C100 mice, except that the APP-C100 was expressed with an additional twelve amino acid residues fused to its amino terminus. The additional twelve amino acid residues consisted of an amino terminal methionine, the flag sequence, and a Ser-Met-Gly sequence that was an artifact of DNA construction. The Flag amino acid sequence is Asp-Tyr-Lys-Asp-Asp-Asp-Asp-Lys (SEQ ID NO:4). The following nucleotide sequence was used to encode the flag sequence and the initiation codon preceding it: 5' ATGGAC-TACA AAGACGATGA CGATAAA 3' (SEQ ID NO:5).

A 4.65 kilobase (kb) DNA fragment containing the dystrophin brain promoter-Flag-C100 fusion gene with the SV40 early region splice and polyadenylation sequences, was isolated. This DNA fragment was microinjected into the pronuclei of fertilized F2 eggs from hybrid (C57BL/6J×SJL/J) mice at DNX (Princeton, N.J.). The microinjected mouse eggs were transferred into the uterus of pseudopregnant females, where they were implanted and were carried to term.

Genetic and Biochemical Characterization

DNA Analysis

Genomic DNA was extracted from samples of mouse tail tissue. The samples were treated with SDS/proteinase K, at 55° C. overnight. Sodium chloride was added to a final concentration of 1.5M, and the mixture was extracted with chloroform. The DNA was precipitated from the aqueous phase with ethanol and resuspended overnight at 4° C.

Starting with 200 ng of DNA, PCR which was carried out for 33 cycles (94° C., 1 min; 50° C., 1 min; 72° C., 3 min). The 5' primer sequence, i.e., 5' GGAGATCTCT GAAGT- GAAGA TGGATG 3' (SEQ ID NO:6) was within the APP-C100 cDNA. The 3' primer 5' GTCACACCAC AGAAGTAAGG TTCC 3' (SEQ ID NO:7) represented sequence within the SV40 splice and polyadenylation region. The predicted 600 bp PCR product was detected in the DNA of 8 of 53 potential transgenic founder mice.

For Southern blots, $^{32}$P-labeled probes containing the SV40 splice and polyadenylation sequence were prepared by the random hexanucleotide priming method. The blots were washed to a maximum stringency of 0.5× SSC at 65° C. with 0.1% SDS. Transgene copy number was estimated by comparing the intensity of a positively hybridizing transgene restriction fragment with that hybridizing with the CDNA for the endogenous growth associated protein GAP-43 gene (Neve et al., *Mol. Brain Res.* 2:177–183 (1987)), which exists as a single copy in the haploid genome. The founder mice and subsequent generations of transgenic mice were backcrossed to C57BL/6J mice.

DNA extracted from the tails of 53 offspring was analyzed for the presence of the Flag-APP-C100 transgene by the PCR, using primers internal to the transgene construct. Eight of the mice were positive for the transgene, and 6 of these 8 produced transgene-positive progeny. Southern blot analysis was used to estimate the transgene copy number in each founder line. Line 18 appeared to have a single copy of the transgene; line six had approximately ten copies; and the remaining lines had 10–20 copies. In subsequent Southern blot analyses of DNA from F1 and F2 progeny, inheritance of the transgene, without rearrangements or changes in copy number, was observed.

Expression of RNA

Total RNA from 100–500 mg of tissue was prepared by a guanidinium thiocyanate procedure (Neve et al., *Mol. Brain Res.* 1:271–280 (1986)). In the final step, the RNA was precipitated with ½ volume of ethanol, which preferentially precipitates RNA but not DNA. One $\mu$g of RNA from each tissue was treated with DNAse I (0.3 U/$\mu$l in a volume of 13.1 $\mu$l) at 37° C. for 20 min to remove possible contaminating DNA. It was then used as a template for RT-PCR (Ivins et al., *J. Neurochem.* 60:626–633 (1993)). The 5' primer, i.e., 5' TGCTTTCAGG AAGATGACAG AATCAG- GACA 3' (SEQ ID NO:8) represented sequence within the dystrophin promoter region that is transcribed and is part of the 5' untranslated region of the transgene transcript. The 3' primer 5' GTCACACCAC AGAAGTAAGG TTCC 3' (SEQ ID NO.9), represented sequence within the SV40 splice and polyadenylation region. These primers were used to generate the predicted PCR product of 650 bp. The identity of the PCR products was confirmed by a Southern blot analysis using a 40-bp antisense oligonucleotide representing sequence internal to the predicted PCR fragment.

RNA from the brains of 6–7 month old Flag-APP-C100 transgenic animals was examined for expression of the transgene. Reverse transcription coupled with RT-PCR was used to amplify an RNA segment predicted to be expressed from the transgene. Using a sense primer representing transcribed sequence within the dystrophin promoter region and an antisense primer within the SV40 splice and polyadenylation sequence, the expected 650 base pair (bp) RT-PCR fragment was observed in all transgenic brain RNAs examined. Expression of the transgene RNA was highest in the brains of mice from transgenic lines 2, 17, and 18.

Expression of Protein

The dystrophin promoter is a weak promoter. It was chosen to drive expression of Flag-APP-C100 because high transgene expression levels potentially could have been lethal, before embryonic development was complete.

A monoclonal antibody to human A$\beta$ (10D5, gift of D. Schenk, Athena Neurosciences, Inc.), which does not react with mouse $\beta$APP, was used to detect Flag-APP-C100 protein in the line 2 mice. This antibody detected the expected 19-kDa band in animals positive for the transgene, but not in transgene-negative littermates.

The APP-C100 protein migrated with an apparent molecular weight of 15 kDa, upon tris-tricine SDS- polyacrylamide (TT-SDS-PAGE). Flag-APP-C100 migrated with an apparent molecular weight of 19 kDa.

Expression of the transgene protein product in the brains of line 18 transgenic mice was demonstrated. Brain tissue was partitioned into cytosolic and membrane fractions, which were analyzed by TT-SDS-PAGE (16.5% gel). The electrophoretic bands were immunoblotted and probed with antibody 369A, an affinity purified antibody prepared against the C-terminal 50 amino acids of APP (Buxbaum et al., *Proc. Nat. Acad. Sci. USA* 87:6003–6006 (1990)). A 19 kDa immunoreactive band was observed in cytosolic and membrane fractions from transgenic, but not control mice.

The immunoblot results were confirmed by immunoprecipitation. The immunoaffinity purified antiserum E1-42 (Cummings et al., *Neuroscience* 48:763–777 (1992)), raised against a peptide representing the 42-amino acid human A$\beta$ fragment, was used to immunoprecipitate C-terminal derivatives of APP from transgenic brain homogenates. The precipitated proteins were subjected to TT-SDS-PAGE and probed with C8, an antibody to the C-terminal 10 amino acids of APP Selkoe et al., *Proc. Natl. Acad. Sci. USA* 85:7341–7345 (1988)). A 19-kDa protein was detected in the cytosolic fraction from brains of transgenic, but not control mice.

Neuropathology Studies

Ages and Numbers of Animals

A total of 160 mice, ranging in age from 8 through 28 months were examined. Included were 88 APP-C100 transgenic mice (including 25 mice over 18 months of age), twenty-seven Flag-APP-C100 mice (seven from line 2, sixteen from line 18, and two from line 17, and one each from lines one and six), 22 non-transgenic control littermates matched for age and sex, and 23 C57BL/6J and SJL/J age-matched controls. Approximately equal numbers of each sex were examined.

Collection of Tissues

The mice were anesthetized by Halothane inhalation and perfused transcardially with a variety of buffers and fixatives which included 0.1M cacodylate buffer, pH 7.4 containing 4% sucrose and 4% paraformaldehyde; 3% glutaraldehyde in 0.1M cacodylate buffer, pH 7.4; 0.1M phosphate buffered saline (PBS), pH 7.4; and 4% paraformaldehyde in PBS, pH 7.4 (Oster-Granite et al., *J. Comp. Neurol.* 169:443–479 (1976)). Following perfusion, sample tissues were placed into fresh fixative overnight. The brains were cut into 2 mm slabs using a coronal brain matrix mold, and the slabs were placed in fresh fixative. The right half of each slab was then dissected to isolate cortex, hippocampus, striatum, cerebellum, and hypothalamus. These regions were cut into 1 mm slabs, processed through graded alcohols to Polybed 812, and stained en bloc with uranyl acetate. Plastic semithin sections (1.0 μm) were collected from each block. In areas selected for study, ultrathin sections were produced for examination in a Zeiss 10 electron microscope.

Hippocampal Formation

In hippocampal formations of the 12 month-old controls, only occasional necrotic pyramidal cells were observed throughout Ammon's horn and only scattered degenerating granule cells were observed in the dentate gyrus. The pyramidal and granule cells of both control strains (C57BL/6J and SJL/J) were approximately the same size and appeared more densely packed than did those of the aged transgenic mice.

Each of the one-year-old Flag-APP-C100 mice examined exhibited numerous degenerating neurons with dystrophic dendrites throughout Ammon's horn and in the dentate gyrus. This neurodegeneration was similar to pathology seen in AD. The one-year-old line 7 (APP-C100) mice did not show this degree of degeneration in the hippocampal formation, although severe AD-like degeneration is seen in 18–28-month-old mice from this line.

Quantitative analyses of cell degeneration in the hippocampal formations of one year old mice revealed significant differences among the groups. Quantitation of degenerating cells in the dentate gyrus of transgenic and control mice revealed significantly more numerous degenerating cells ($p<0.0015$, ANOVA) in Flag-APP-C100 mice than in the nontransgenic controls and APP-C100 mice. No significant differences between the sexes were observed.

Numerous pyramidal cells in various states of degeneration were found throughout the dentate gyrus and Ammon's horn in an exemplary 23 month-old, and an exemplary 28 month-old male APP-C100 mouse, respectively, and with lesser magnitude in a 24 month-old female APP-C100 mouse, as well. Degeneration of varying degree was detected in all transgenic progeny of age over 18 months, derived from line seven APP-C100 founders. It was not determined whether homozygous individuals exhibit a comparable degree of pathology at an earlier age than do heterozygous individuals. The cell bodies of the pyramidal cells of an exemplary 23 month-old transgenic mouse appeared to be smaller than those of an exemplary 28 month-old transgenic.

The pyramidal cell layers in an exemplary line one and an exemplary line 17 14.5 month-old Flag-APP-C100 transgenic male mouse were compared. Numerous degenerating pyramidal cells with dystrophic dendrites were readily detected in Ammon's horn of the line one Flag-APP-C100 transgenic mouse, while a similar but less severe degeneration was visible in the line 17 Flag-APP-C100 mouse.

In hippocampal formations of the control aged C57BL/6J and SJL/J mice, only occasional necrotic pyramidal cells throughout Ammon's horn was observed at 22 and 24 months, respectively. The pyramidal cells of both control strains were approximately the same size and appeared more densely packed than those of the aged transgenic animals.

Secondary Lysosomes

A previously-reported feature of the APP-C100 transgenic mice, detected as early as 4.5 months of age, was the appearance of oddly shaped secondary lysosomes which were immunoreactive with antibodies directed against portions of APP-C100 (Kammesheidt et al., supra). These inclusions resembled strongly those that identified earlier in affected regions of AD brain (Benowitz et al., *Exptl. Neurol.* 106:237–250 (1989). In the older groups of transgenic animals, these structures took the form of abundant deposits of dense, granular material in many of the pyramidal cells of the hippocampal formation. The granular accumulations are more prominent in neurons in the molecular layer of Ammon's horn.

Both degenerating and relatively healthy neurons contained numerous accumulations of secondary lysosomal structures. In contrast to the neurons in the aged normal mice, both normal and degenerating neurons in the transgenic mice had, in close apposition, cells whose nuclear morphology closely resembled that of microglial cells. Dense cells, which upon ultrastructural examination were shown to have the morphologic characteristics of microglia laden with debris, lay next to blood vessels in the transgenic mouse brains. In contrast, few degenerating neurons or duets of neurons with adjacent microglial cells were detected in the neuropil of the aged SJL mice.

Ultrastructural analysis of the inclusions in the pyramidal cells of the aged APP-C100 mice revealed that the characteristic inclusions prominent in the thin sections were oddly shaped secondary lysosomes, more abundant in the cell cytoplasm surrounding the nucleus than in dendritic or axonal processes of the cells. These lysosomes had a distinctly granular appearance and often contained material that was clear and lipid-like.

The lysosomal accumulations of the Flag-APP-C100 mice were, in general, more densely granular in appearance in the less severely affected mice, such as the line 17 founder, and more heterogeneous in appearance in the line one founder mouse. The morphology of these inclusions is fairly distinct within each line. The inclusions in Flag-C100-APP mice were more heterogeneous than were those in the APP-C100 mice. Also, they were abundant at much earlier ages than were the inclusions of the APP-C100 mice. The inclusions in the APP-C100 mice were as abundant at one year of age as were the inclusions in aged normal C57BL/6J and SJL/J mice at two years of age. Thus, the secondary lysosomes occurred to some extent during normal aging of C57BL/6J and SJL/J mice, but were morphologically abnormal and more abundant at earlier ages, in the transgenic mice.

Cytoskeletal and Synaptic Degeneration

Examination of the pyramidal cell layer of the aged APP-C100 mice revealed numerous degenerating synapses, axons containing increased numbers of neurofilaments relative to those of control mice, and membranous whorls in axonal and dendritic processes. In addition, secondary lysosomal inclusions in both dendritic and axonal processes near the cell body in numerous neurons in the pyramidal cell layer of these animals were frequently observed. Microglia laden with debris were found adjacent to large venous vessels that contained thickened basement membranes.

The line one Flag-APP-C100 transgenic mice contained an abundance of necrotic pyramidal cells, microglial cells laden with debris, and degenerating synaptic complexes. In other Flag-APP-C100 transgenic mice, the extent of the degenerative process seemed to correlate with the degree of expression of the transgene. Even in the less severely affected Flag transgenic mice, however, the degree of degeneration in Ammon's horn at 14.5 months of age was similar to that observed in the aged APP-C100 transgenic mice at 28 months. A similar magnitude of degeneration was observed in the dentate gyrus of each animal examined.

The Flag-APP-C100 transgenic mice displayed the synaptic damage, neuronal death, disruption of the neuronal cytoskeleton, and lysosomal abnormalities seen in APP-C100 mice, but they did so at a much younger age. The phenotype of these animals indicates that APP-C100 is a critical component of the molecular mechanism of AD neurodegeneration.

Behavioral Studies

Ages and Numbers of Animals

Seventy-eight mice at approximately one year of age were tested behaviorally. Both APP-C100 and Flag-APP-C100 mice were included in the study, to determine whether the neuropathological differences between them would be reflected in differences in cognitive function. The mice tested included: 24 males and 21 females from APP-C100 line 7; 11 males and 8 females from Flag-APP-C100 line 2; 7 males and 7 females from Flag-APP-C100 line 18. At the time of testing, the mice were between 12 and 14.5 months of age, except 4 mice from APP-C100 line 7, that were 6 months old.

The mice were housed 3 or 4 mice per cage, separated by sex, and maintained in a room with a 12 hour-12 hour light-dark cycle. For and water were available ad libitum except during testing. The mice were first habituated for about one week. At the end of the week, the mice were subjected to a neurologic battery that included testing of righting, grasping, and placing of reflexes. The mice were then subjected to three weeks of swim navigation testing. Activity measurements were carried out navigation tests. The navigation tests. The experimenter was blind to the transgenic status of the mice during testing.

Swim Navigation Tests

All of the navigation tasks were conducted in a 180 cm diameter white circular pool surrounded by distal cues (Berger-Sweeney et al. (*Behav. Neurosci.* 109:859–873 (1995)). Water temperature was 21°–23° C. A 103-cm diameter ring was placed in the pool to adapt the size of the pool for testing mice. A 55-cm diameter ring was used for pretraining trials. The platform, a 6×6 cm clear acrylic square, was always placed 15 cm from the edge of the ring in one of four quadrants defined by four equally spaced, arbitrarily designated start points (N, S, E, and W).

The testing schedule consisted of one day of pretraining, five days of cued trials, five days of spatial trials followed by a probe trial, and four days of reversal trials followed by a probe (see Berger-Sweeney et al., 1995 (supra); Berger-Sweeney et al., *J. Neurosci.* 14:4507–4519 (1994)). For the reversal task, the pool was set up and trials were run in a manner identical to that of the spatial task, except that the invisible platform was moved to a new location. The day after completion of the reversal trials, the platform was removed from the pool and again each mouse was given a probe trial for 60 seconds. All navigation data were tracked and analyzed using an HSV video tracking system (HSV Image, Hampton, England). Additional analyses were carried out using computer software (Wolfer et al. *J. Neurosci.* 41:65–74 (1992)).

All nontransgenic animals, which were age-matched littermates of the transgenic animals, were combined into a single control group. Controls were compared to line 7 APP-C100, or to line 2 and line 18 Flag-APP-C100 mice. All data were analyzed statistically using repeated measures analysis of variance (ANOVA). Fisher's protected least significant difference (PLSDs) were used, posthoc (Berger-Sweeney et al. (1995). Behavioral data from Flag-APP-C100 transgenic lines 2 and 18 were not significantly different. Therefore, those data were combined for purposes of the following discussion.

Both control mice and transgenic mice ranged in color from black to brown to agouti. All but three mice exhibited normal righting, grasping and placing reflexes. The three mice that failed the neurological battery were APP-C100 transgenic mice. These mice appeared arthritic and hunched over, and were unable to perform the navigation tasks. In addition, there were two mice (one nontransgenic and one APP-C100 transgenic) that displayed tumors during the course of the navigation tasks. These tumors were not detectable throughout behavioral testing and did not impair the abilities of these mice to swim.

Dark-cycle Activity

Figure 1B:
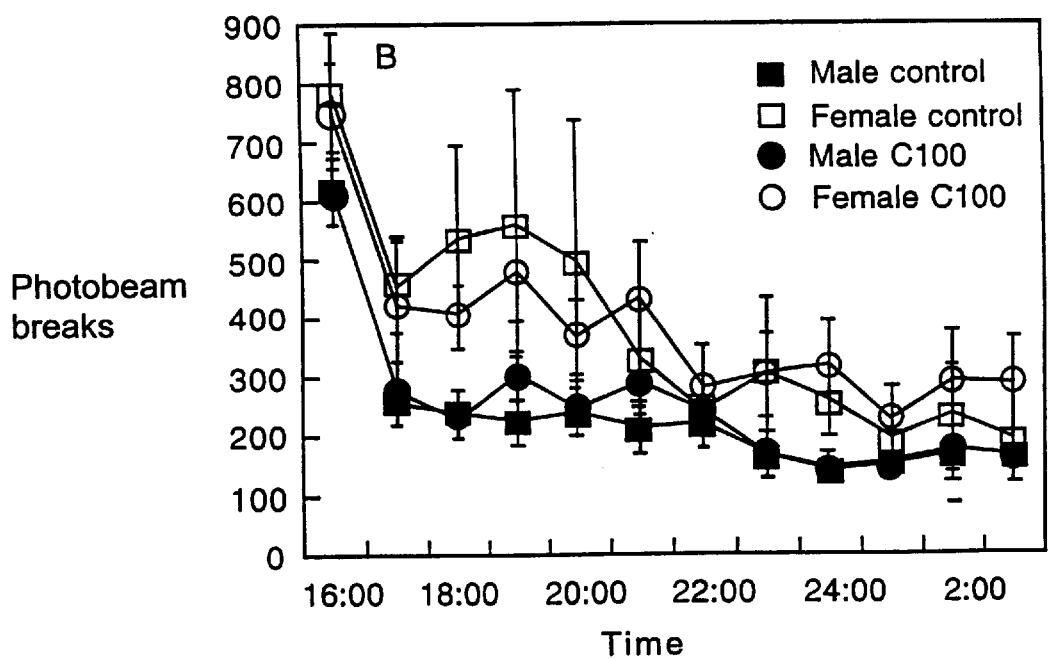
FIG. 1B is a graph showing data on spontaneous locomotor activity of control and APP-C100 mice. The number of photobeam breaks made over a 12-hour period is shown. Closed squares, male control; open squares, female control; closed circles male APP-C100; open circles, female APP-C100.

In all of the groups of mice, activity levels, as measured by photobeam breaks, were high during the first hour and then decreased sharply over the next 11 hours (FIGS. 1A and 1B). There were no significant differences among the groups when controls were compared to the Flag-APP-C100 groups [$F(3,54)=1.23$, non-significant (nos)] or to the APP-C100 groups [$F(3,50)=1.54$,ns]. However, when the groups were combined by sex (i.e. control and transgenic females were combined), it became apparent that female mice were significantly more active than male mice throughout the dark cycle, particularly during the first six hours [$F(1,52)=4.77$, ns].

Cued Navigation Task

All groups performed the cued task similarly. Path length to find the visible platform decreased from session 1 to session 5 in all groups (FIGS. 2A–2F). There were no significant differences in path length data among the different groups or between the sexes [control vs. Flag-APP-C100 mice, $F(3,54)=1.36$, ns; and control vs. APP-C100 mice, $F(3,52)=0.93$, ns]. Similarly, latencies to find the hidden platform decreased steadily over the five sessions, but exhibited no significant differences among the different groups or between the sexes [control vs. Flag-APP-C100 mice, $F(3,54)=0.61$, ns and control vs. APP-C100 mice, $F(3,52)=0.88$, ns; data not shown].

Spatial Navigation Task

In all groups, path lengths decreased significantly across the sessions as the mice learned the task (FIGS. 2B and 2E. In sessions 6–8, path lengths decreased sharply. Sessions 9 and 10 (the last two days of spatial navigation testing) represented asymptotic performance in all of the groups. Path lengths to find the platform differed between the control and Flag-APP-C100 groups [$F(3,54)=4.03,p<0.05$]. The Flag-APP-C100 females had longer path lengths than did male control and male Flag-APP-C100 mice; these differences were significantly different in post-hoc tests in sessions 8, 9 and 10 (PLSDs all $p<0.05$). Path lengths did not differ significantly between the control and APP-C100 groups [$F(3,52)=1.43$, ns]. The data, however, showed the same trend as those for the Flag-APP-C100 mice, with the longest path lengths exhibited by transgenic females.

No significant differences in latencies to find the hidden platform were observed in any group. Control mice did not differ significantly from Flag-APP-C100 [$F(3,54)=0.21$, ns] nor from APP-C100 [$F(3,52)=0.57$, ns] mice.

Figure 3A:
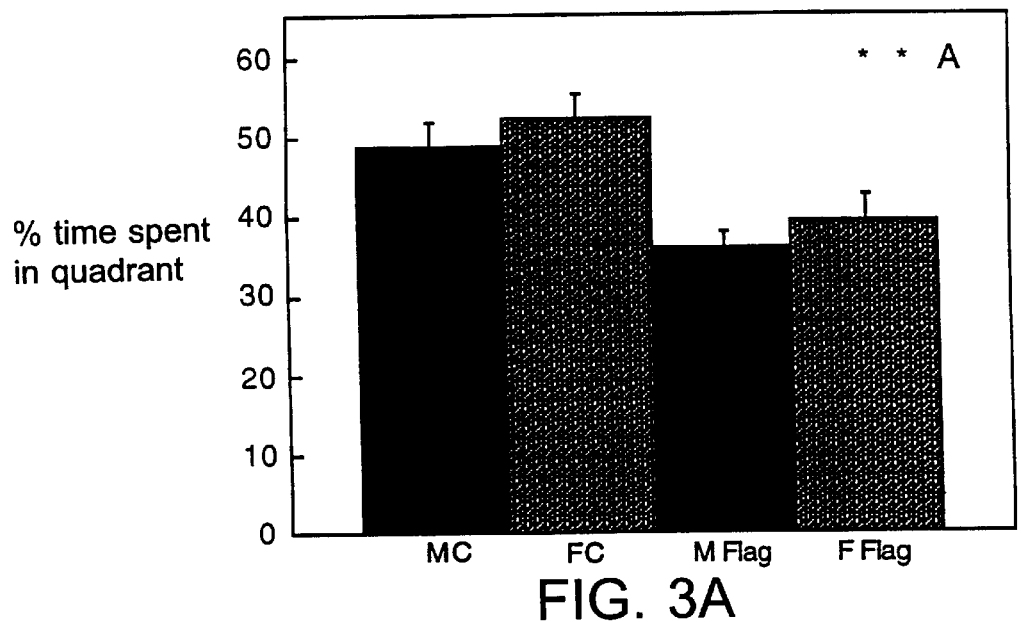
FIG. 3A is a graph showing percent time spent by control and flag mice during a 60-second probe trial in the quadrant of the pool where the platform had formerly been located during spatial trials. The ** indicates statistical significance at $p<0.01$ (ANOVA).
Figure 3B:
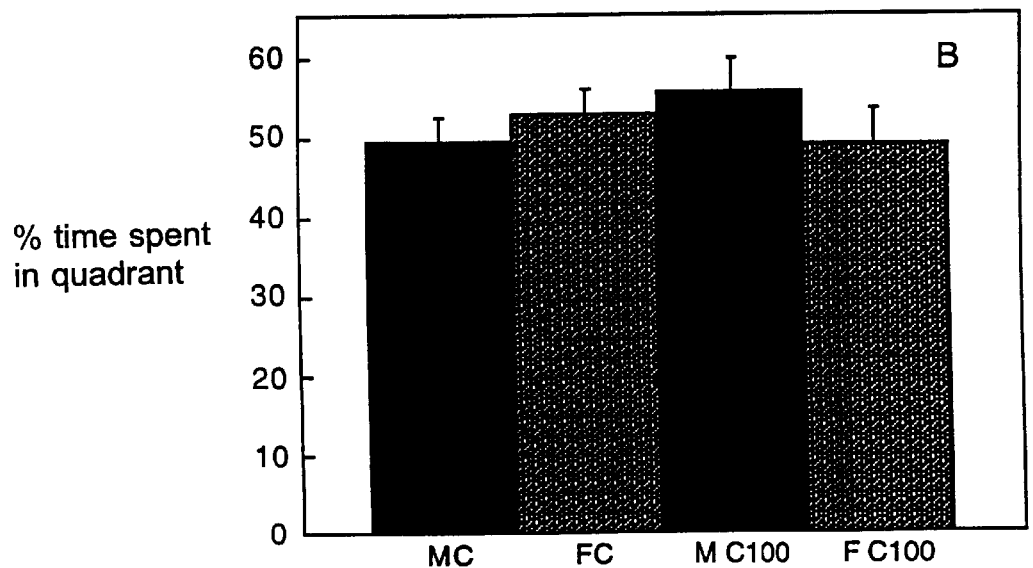
FIG. 3B is a graph showing percent time spent by control and APP-C100 mice during a 60-second probe trial in the quadrant of the pool where the platform had formerly been located during spatial trials.
Figure 4:
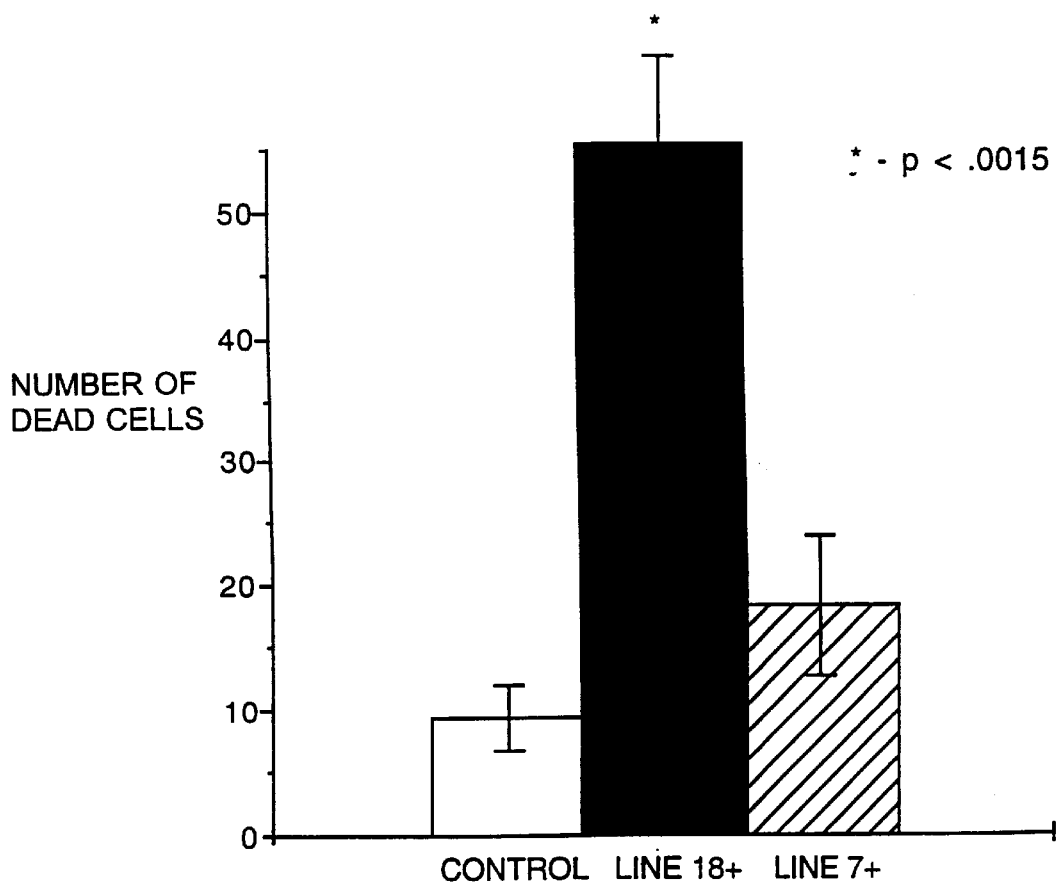
FIG. 4 is a graph showing quantitation of dead cells in the dentate gyrus of six control mice, five Flag-APP-C100 line 18 transgenic mice, and five APP-C100 line 7 transgenic mice, all 12–14 months of age. The * indicates statistical significance for line 18 relative to line 7 and controls, at $p<0.015$ (ANOVA).

Probe Trial #1 The probe trial (in which the platform was removed from the tank) which followed session 10 of the spatial navigation trial suggested that the mice had learned, to some degree, the position of the platform, i.e., all mice spent more than chance (25%) levels of time in the quadrant that formerly contained the platform. However, when control and Flag-APP-C100 mice were compared, significant differences in the amount of time spent in the former platform quadrant were revealed [FIG. 3A; $F(3,54)=5.35$, $p<0.01$]. Flag-APP-C100 females and males spent less time in the quadrant that formerly contained the platform (38.7±3.7% and 36.7±2.1%, respectively) than did control mice, who spent about 50% of the time in the former platform quadrant. There were no significant differences between the control and APP-C100 groups in the amount of time spent in the quadrant formerly containing the platform (FIG. 3B).

Reversal Navigation Task In the reversal trials, the hidden platform was moved to a different position from that in the spatial trials. Performance was examined as the mouse unlearned the old position and relearned a new platform position. For all groups of mice, the path lengths to find the new hidden platform position decreased steadily from session 11 to session 14. Path lengths, however, differed significantly between control and Flag-APP-C100 groups [FIG. 2C; F(3,54)=3.3, p<0.05]. Flag-APP-C100 females exhibited consistently longer path lengths than the other groups in session 12–14 (PLSDs all p<0.05). The male Flag-APP-C100 mice exhibited consistently the shortest path lengths; these differences reached statistical significance in session 12. Path lengths in the control and APP-C100 groups did not differ significantly across the sessions [FIG. 2F; F(3,52)=1,22, ns].

Latencies to find the hidden platform decreased during the course of the reversal task sessions in all groups. Reversal latencies differed when the controls were compared to the Flag-APP-C100 groups [F (3,54)=3.78, p<0.05]. Latencies in the control males and the Flag-APP-C100 females were significantly longer than in those in control females and Flag-APP-C100 males. Latencies to find the hidden platform did not differ between controls and the APP-C-100 group, consistent with the path length data [F(3,52)=2.33, ns].

Probe Trial #2

The second probe trial, which followed the reversal task, was used to examine navigation patterns following removal of the platform from the new reversal quadrant. The mice spent more than chance (25%) levels of time in the quadrant that formerly contained the platform (data not shown). Overall, the mice spent about 42% of the time in the quadrant that formerly contained the platform, which was less than the time spent in the former platform quadrant following the first probe trial (after the spatial task). There were no significant differences in performance when controls were compared to Flag-APP-C100 mice [F(3,54)=0.64, ns] or to APP-C100 mice [F(3,52)=2.11, ns; data not shown].

Analyses of the navigation data showed that the mice were swimming almost continuously during the navigation trials, and that they were not stalling. The swim speeds did not differ significantly between control and APP-C100 mice during any of the three navigation tasks. Flag-APP-C100 females swam significantly faster than did the other groups on virtually all days of the cued navigation trials. These swim speed differences, however, were not apparent during either spatial or reversal navigation trials. All groups of mice spent progressively less time in the peripheral (outer ⅓rd) zone of the pool during the course of the sessions. The female and male Flag-APP-C100 groups spent virtually identical amounts of time in the peripheral zone. The time spent in the peripheral zone of the pool did not differ significantly between control and APP-C100 mice during any of the three navigation tasks (data not shown).

All groups spent progressively more time in the quadrant-containing platform as the sessions of the spatial and reversal tasks proceeded (data not shown). When control groups were compared to the Flag-APP-C100 groups, however, there were significant differences between the groups [F(3, 54)=3.53 p<0.05]. Flag-APP-C100 females spent less time in the quadrant containing the platform throughout the spatial task. However, during the reversal task, this trend disappeared and there were no significant differences among the groups [F(3,54)=2.00, ns]. There were no significant differences between the control and APP-C100 groups [F(3, 52) =0.12, ns for the spatial task and F(3,52)=1.6, ns for the reversal task].

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 105 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

```
Ile  Ser  Glu  Val  Lys  Met  Asp  Ala  Glu  Phe  Arg  His  Asp  Ser  Gly  Tyr
 1              5                        10                       15

Glu  Val  His  His  Gln  Lys  Leu  Val  Phe  Phe  Ala  Glu  Asp  Val  Gly  Ser
                20                   25                       30

Asn  Lys  Gly  Ala  Ile  Ile  Gly  Leu  Met  Val  Gly  Gly  Val  Val  Ile  Ala
           35                       40                       45

Thr  Val  Ile  Val  Ile  Thr  Leu  Val  Met  Leu  Lys  Lys  Lys  Gln  Tyr  Thr
     50                       55                  60

Ser  Ile  His  His  Gly  Val  Val  Glu  Val  Asp  Ala  Ala  Val  Thr  Pro  Glu
65                        70                       75                       80

Glu  Arg  His  Leu  Ser  Lys  Met  Gln  Gln  Asn  Gly  Tyr  Glu  Asn  Pro  Thr
                85                        90                       95
```

```
          Tyr  Lys  Phe  Phe  Glu  Gln  Met  Gln  Asn
                        100                      105
```

(2) INFORMATION FOR SEQ ID NO:2:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...351
        (D) OTHER INFORMATION:

(xi) SEQUENCE DESCRIPTION: SEQ ID NO:2:

```
ATG  GAC  TAC  AAA  GAC  GAT  GAC  GAT  AAA  TCG  ATG  GGG  ATC  TCT  GAA  GTG         48
Met  Asp  Tyr  Lys  Asp  Asp  Asp  Asp  Lys  Ser  Met  Gly  Ile  Ser  Glu  Val
 1                   5                        10                      15

AAG  ATG  GAT  GCA  GAA  TTC  CGA  CAT  GAC  TCA  GGA  TAT  GAA  GTT  CAT  CAT         96
Lys  Met  Asp  Ala  Glu  Phe  Arg  His  Asp  Ser  Gly  Tyr  Glu  Val  His  His
               20                       25                       30

CAA  AAA  TTG  GTG  TTC  TTT  GCA  GAA  GAT  GTG  GGT  TCA  AAC  AAA  GGT  GCA        144
Gln  Lys  Leu  Val  Phe  Phe  Ala  Glu  Asp  Val  Gly  Ser  Asn  Lys  Gly  Ala
          35                       40                        45

ATC  ATT  GGA  CTC  ATG  GTG  GGC  GGT  GTT  GTC  ATA  GCG  ACA  GTG  ATC  GTC        192
Ile  Ile  Gly  Leu  Met  Val  Gly  Gly  Val  Val  Ile  Ala  Thr  Val  Ile  Val
 50                       55                        60

ATC  ACC  TTG  GTG  ATG  CTG  AAG  AAG  AAA  CAG  TAC  ACA  TCC  ATT  CAT  CAT        240
Ile  Thr  Leu  Val  Met  Leu  Lys  Lys  Lys  Gln  Tyr  Thr  Ser  Ile  His  His
 65                       70                       75                       80

GGT  GTG  GTG  GAG  GTT  GAC  GCC  GCT  GTC  ACC  CCA  GAG  GAG  CGC  CAC  CTG        288
Gly  Val  Val  Glu  Val  Asp  Ala  Ala  Val  Thr  Pro  Glu  Glu  Arg  His  Leu
                    85                       90                       95

TCC  AAG  ATG  CAG  CAG  AAC  GGC  TAC  GAA  AAT  CCA  ACC  TAC  AAG  TTC  TTT        336
Ser  Lys  Met  Gln  Gln  Asn  Gly  Tyr  Glu  Asn  Pro  Thr  Tyr  Lys  Phe  Phe
               100                      105                      110

GAG  CAG  ATG  CAG  AAC  TAG                                                          354
Glu  Gln  Met  Gln  Asn
               115
```

(2) INFORMATION FOR SEQ ID NO:3:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:3:

```
Met  Asp  Tyr  Lys  Asp  Asp  Asp  Asp  Lys  Ser  Met  Gly  Ile  Ser  Glu  Val
 1                   5                        10                      15

Lys  Met  Asp  Ala  Glu  Phe  Arg  His  Asp  Ser  Gly  Tyr  Glu  Val  His  His
               20                       25                       30

Gln  Lys  Leu  Val  Phe  Phe  Ala  Glu  Asp  Val  Gly  Ser  Asn  Lys  Gly  Ala
          35                       40                        45

Ile  Ile  Gly  Leu  Met  Val  Gly  Gly  Val  Val  Ile  Ala  Thr  Val  Ile  Val
 50                       55                        60

Ile  Thr  Leu  Val  Met  Leu  Lys  Lys  Lys  Gln  Tyr  Thr  Ser  Ile  His  His
 65                       70                       75                       80
```

```
Gly Val Val Glu Val Asp Ala Ala Val Thr Pro Glu Glu Arg His Leu
            85                  90                      95

Ser Lys Met Gln Gln Asn Gly Tyr Glu Asn Pro Thr Tyr Lys Phe Phe
            100                 105                 110

Glu Gln Met Gln Asn
            115
```

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Asp Tyr Lys Asp Asp Asp Asp Lys
 1               5
```

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

ATGGACTACA AAGACGATGA CGATAAA                                  27

( 2 ) INFORMATION FOR SEQ ID NO:6:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GGAGATCTCT GAAGTGAAGA TGGATG                                   26

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GTCACACCAC AGAAGTAAGG TTCC                                      24

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

TGCTTTCAGG AAGATGACAG AATCAGGACA                           30

( 2 ) INFORMATION FOR SEQ ID NO:9:

-continued ( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:9:

GTCACACCAC AGAAGTAAGG TTCC    24

---

Other embodiments of the invention are within the following claims.

What is claimed is:

1. A transgenic mouse whose genome comprises a DNA sequence encoding a polypeptide comprising the Flag peptide of SEQ ID NO: 4 fused to the amino terminus of an APP-C100 polypeptide directly or by 1 to 5 intervening amino acid residues, said DNA sequence operably linked to expression control sequences active in brain, and expressing said DNA sequence, wherein expression of the DNA sequence results in said mouse exhibiting degeneration of neurons and synapses in the hippocampal formation and exhibiting cognitive impairment.

2. The mouse of claim 1, wherein said APP-C100 polypeptide consists of an amino acid sequence selected from the group consisting of:

(a) (SEQ ID NO:1);
(b) amino acids 2–105 of (SEQ ID NO:1);
(c) amino acids 3–105 of (SEQ ID NO:1);
(d) amino acids 4–105 of (SEQ ID NO:1);
(e) amino acids 5–105 of (SEQ ID NO:1); and
(f) amino acids 6–105 of (SEQ ID NO:1).

3. The mouse of claim 2, wherein said APP-C100 polypeptide consists of (SEQ ID NO:1).

4. The mouse of claim 1, wherein said recombinant DNA sequence encodes a polypeptide consisting of (SEQ ID NO:3).

5. The mouse of claim 4, wherein said recombinant DNA sequence consists of (SEQ ID NO:2).

6. The mouse of claim 1, wherein said expression control sequences include a brain-specific promoter.

7. The mammal of claim 6, wherein said brain-specific promoter is a dystrophin promoter.

8. A method for enhancing neurodegeneration in the brain of a transgenic mouse, said method comprising:

a) obtaining an isolated DNA sequence encoding a polypeptide comprising the Flag peptide of SEQ ID NO: 4 fused to the amino terminus of an APP-C100 polypeptide directly or by 1 to 5 intervening amino acid residues, said DNA sequence operably linked to expression control sequences active in brain;

b) introducing said DNA sequence into a mouse embryo thereby producing a transgenic mouse embryo whose genome comprises said DNA sequence;

c) developing said transgenic mouse embryo into said mouse, wherein expression of the DNA sequence results in an earlier onset of neurodegeneration in the brain of said transgenic mouse as compared to a control transgenic mouse that expresses APP C-100 without said Flag peptide being fused thereto.

9. A method for enhancing cognitive impairment in the brain of a transgenic mouse, said method comprising:

a) obtaining an isolated DNA sequence encoding a polypeptide comprising the Flag peptide of SEQ ID NO: 4 fused to the amino terminus of an APP-C100 polypeptide directly or by 1 to 5 intervening amino acid residues, said DNA sequence operably linked to expression control sequences active in brain;

b) introducing said DNA sequence into a mouse embryo thereby producing a transgenic mouse embryo whose genome comprises said DNA sequence;

c) developing said transgenic mouse embryo into said mouse, wherein expression of the DNA sequence results in an increase in the intensity of cognitive impairment in said transgenic mouse as compared to a control transgenic mouse that expresses APP C-100 without said Flag peptide being fused thereto.

10. A method for identifying compounds that inhibit neurodegeneration in Alzheimer's Disease, said method comprising;

a) providing a transgenic mouse whose genome comprises a DNA sequence encoding a polypeptide comprising the Flag peptide of SEQ ID NO: 4 fused to the amino terminus of an APP-C100 polypeptide directly or by 1 to 5 intervening amino acid residues, said DNA sequence operably linked to expression control sequences active in brain, and expressing said DNA sequence, wherein expression of the DNA sequence results in said mouse exhibiting degeneration of neurons and synapses in the hippocampal formation and exhibiting cognitive impairment;

b) administering to said mouse a candidate compound; and c) assaying for a decrease in neurodegeneration in the brain of said mouse as compared to neurodegeneration in the brain of a mouse of step a) not administered the compound.

11. A method for identifying compounds that inhibit cognitive impairment in Alzheimer's Disease, said method comprising;

a) providing a transgenic mouse whose genome comprises a DNA sequence encoding a polypeptide comprising the Flag peptide of SEQ ID NO: 4 fused to the amino terminus of an APP-C100 polypeptide directly or by 1 to 5 intervening amino acid residues, said DNA sequence operably linked to expression control sequences active in brain, and expressing said DNA sequence, wherein expression of the DNA sequence results in said mouse exhibiting degeneration of neurons and synapses in the hippocampal formation and exhibiting cognitive impairment;

b) administering to said mouse a candidate compound; and c) assaying for a decrease in cognitive impairment in the brain of said mouse as compared to cognitive impairment in the brain of a mouse of step a) not administered the compound.

\* \* \* \* \*